(12) United States Patent
Bordelon

(10) Patent No.: US 7,542,139 B2
(45) Date of Patent: *Jun. 2, 2009

(54) METHOD AND APPARATUS FOR DETERMINING CHARACTERISTICS OF PARTICLES IN A FLUID SAMPLE

(75) Inventor: Michael Bordelon, Saint Martinville, LA (US)

(73) Assignee: Core Laboratories LP, Houston, TX (US)

( * ) Notice: Subject to any disclaimer, the term of this patent is extended or adjusted under 35 U.S.C. 154(b) by 221 days.

This patent is subject to a terminal disclaimer.

(21) Appl. No.: 11/487,724

(22) Filed: Jul. 17, 2006

(65) Prior Publication Data

US 2007/0035738 A1 Feb. 15, 2007

Related U.S. Application Data

(63) Continuation-in-part of application No. 10/742,359, filed on Dec. 19, 2003, now Pat. No. 7,079,242.

(51) Int. Cl.
*G01N 15/02* (2006.01)

(52) U.S. Cl. .................................................... 356/335
(58) Field of Classification Search .......... 356/335–343
See application file for complete search history.

(56) References Cited

U.S. PATENT DOCUMENTS

| | | | |
|---|---|---|---|
| 4,606,631 A * | 8/1986 | Anno et al. | 356/39 |
| 4,747,685 A * | 5/1988 | Suzuki | 356/36 |
| 5,134,445 A * | 7/1992 | Toge | 356/336 |
| 5,420,040 A | 5/1995 | Anfindsen et al. | |
| 5,969,237 A | 10/1999 | Jones et al. | |
| 6,049,381 A * | 4/2000 | Reintjes et al. | 356/335 |
| 6,087,662 A | 7/2000 | Wilt et al. | |
| 6,091,502 A * | 7/2000 | Weigl et al. | 356/416 |
| 6,501,072 B2 | 12/2002 | Mullins et al. | |
| 7,242,474 B2 * | 7/2007 | Cox et al. | 356/338 |
| 2003/0033866 A1 | 2/2003 | Diakonov et al. | |
| 2003/0064505 A1 * | 4/2003 | Hartig | 435/287.1 |

FOREIGN PATENT DOCUMENTS

| | | |
|---|---|---|
| GB | 2 371 858 | 8/2002 |
| WO | WO 99/51963 | 10/1999 |
| WO | WO 00/46586 | 8/2000 |

* cited by examiner

*Primary Examiner*—Hoa Q Pham
(74) *Attorney, Agent, or Firm*—Mossman, Kumar & Tyler, PC

(57) ABSTRACT

A system for determining a parameter of interest of at least one particle in a sample of a fluid obtained from a formation, comprises a view cell containing at least a portion of the sample and at least one window for viewing the sample. A light source illuminates the sample. An imaging system captures at least one image of the illuminated sample. A program executing a set of instructions on a computer analyzes the at least one image and generates an output related to at least one parameter of interest of the at least one particle in said sample.

23 Claims, 2 Drawing Sheets

METHOD AND APPARATUS FOR DETERMINING CHARACTERISTICS OF PARTICLES IN A FLUID SAMPLE

CROSS-REFERENCE TO RELATED APPLICATIONS

This application is a continuation-in-part of U.S. patent application Ser. No. 10/742,359, filed on Dec. 19, 2003, now U.S. Pat. No. 7,079,242.

FIELD OF THE INVENTION

This invention generally relates to fluid sample analysis. More specifically this invention relates to a method and apparatus for determining characteristics of particles in a fluid sample.

BACKGROUND OF THE INVENTION

Problems encountered in crude oil production include the precipitation and/or agglomeration of particles or substances in solution and/or in suspension in the produced formation fluid. The term particles, is defined herein includes, but is not limited to solid particles, emulsion droplets, and gas bubbles. Asphaltenes are examples of solid particle components of crude oil that are often found in colloidal suspension in the formation fluid. If for any reason the colloidal suspension becomes unstable, such as with a drop in fluid pressure, the colloidal particles will precipitate, stick together and, especially in circumstances where the asphaltenes include resins, plug the well. Asphaltene precipitation during production causes severe problems. Plugging of tubing and surface facilities disrupts production and adds cost. Plugging of the formation itself is very difficult and expensive to reverse, especially for a deep water well.

Asphaltenes can precipitate from crude oils during production of the crude oil due to a drop in pressure. Crude oils which are somewhat compressible are particularly susceptible to this effect because the reduction in dielectric constant per unit volume which accompanies fluid expansion causes the asphaltene suspension to become unstable. The onset of asphaltene precipitation is difficult to predict, and when asphaltene plugging happens, it usually happens unexpectedly. Advance warning of asphaltene precipitation based on laboratory testing of formation fluid according to present techniques, while useful, is not optimally reliable.

Formation gas may be contained in solution in the produced formation fluid and may come out of solution as the fluid pressure is reduced during transit of the fluid out of the well.

Attempts have been made to determine the onset of the particle precipitation, particularly asphaltenes. U.S. Pat. No. 5,969,237 to Jones et al. describes a system for detecting scattered acoustic energy to determine particle size distribution of asphaltene particles. U.S. Pat. No. 6,087,662 to Wilt et al. uses mid-range infra red absorption spectroscopy to determine asphaltene concentrations in hydrocarbon feed. U.S. Pat. No. 5,420,040 to Anfindsen et al. provides a system to measure changes in the conductivity or capacitance of a petroleum fluid for determining asphaltene precipitation in the fluid.

All of the prior art systems infer particle precipitation and other related characteristics from related physical measurements. There is a demonstrated need for a system to view and analyze the particles to more definitively determine the characteristics of the particles.

SUMMARY OF THE INVENTION

In aspects, the present invention includes a method and system for determining characteristics of particles in a fluid sample. In one aspect of the present invention, a system for determining a parameter of interest of at least one particle in a sample fluid includes a view cell containing at least a portion of the sample, an imaging system captures at least one image of the illuminated sample, and a computer that analyzes the images to determine one or more parameter of interests of the particles in the sample. A light source can be used to illuminate the fluid sample.

In some embodiments, the device includes a plurality of pumps that flow sample fluid across the view cell. In one arrangement, two controllable pumps cooperate to flow the sample fluid. In another arrangement, a third pump is used to supply a second fluid into the sample fluid. Such an arrangement can be used in connection with a titration or fluid compatibility test. In another arrangement, a filtering element can be used to capture particles flowing out of the view cell. As is known, the captured material can be used in connection with the analysis of the fluid sample.

It should be understood that examples of the more important features of the invention have been summarized rather broadly in order that the detailed description thereof that follows may be better understood, and in order that the contributions to the art may be appreciated. There are, of course, additional features of the invention that will be described hereinafter and which will in some cases form the subject of the claims appended hereto.

BRIEF DESCRIPTION OF THE DRAWINGS

The novel features which are believed to be characteristic of the invention, both as to organization and methods of operation, together with the objects and advantages thereof, will be better understood from the following detailed description and the drawings wherein the invention is illustrated by way of example for the purpose of illustration and description only and are not intended as a definition of the limits of the invention, wherein.

DESCRIPTION OF THE PREFERRED EMBODIMENTS

The present invention is a method and system for determining characteristics, also called parameters of interest, of particles in a fluid sample. To the extent that the following description is specific to a particular embodiment or a particular use of the invention, this is intended to be illustrative and is not to be construed as limiting the scope of the invention.

Figure 1A:
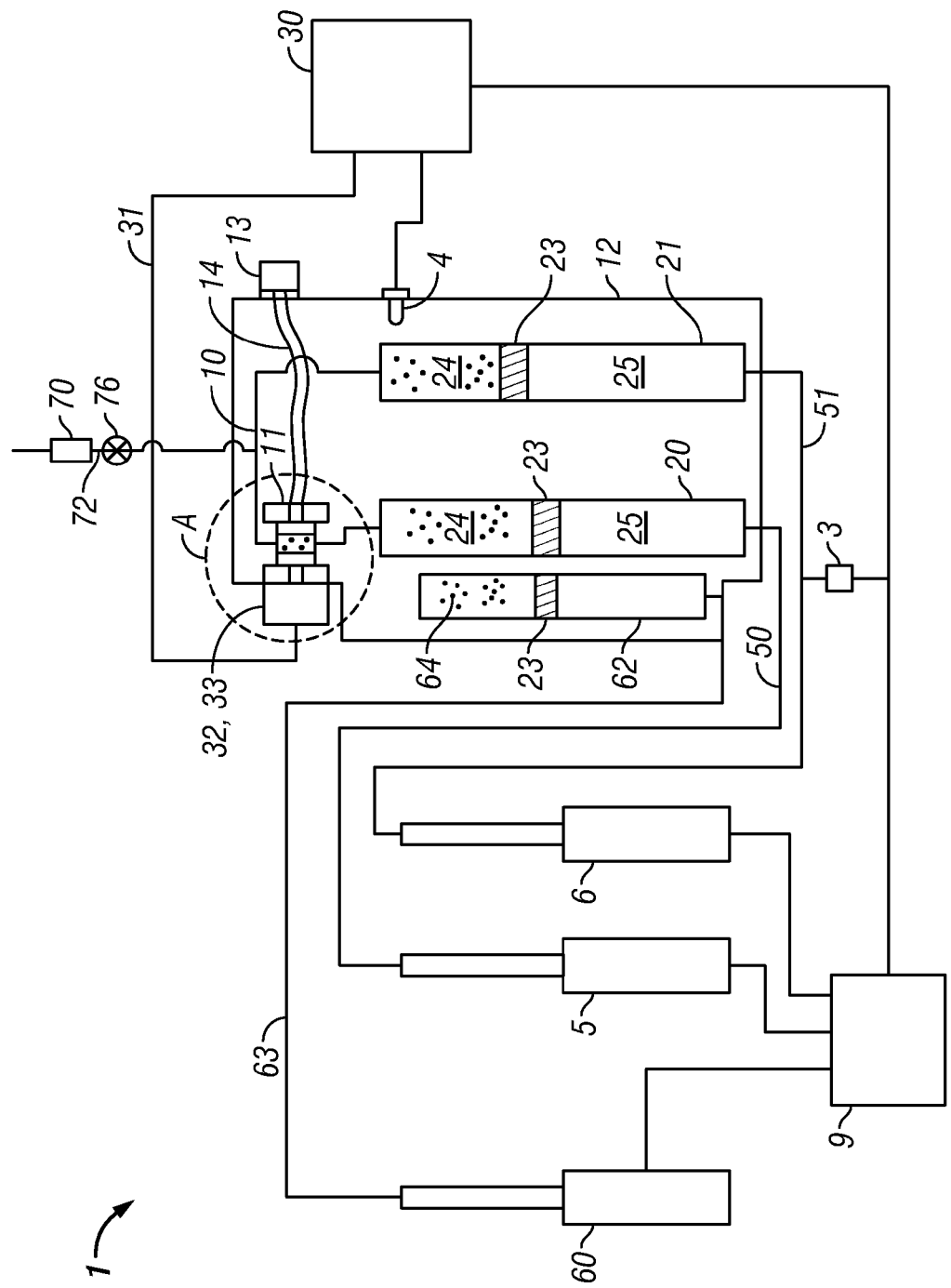
FIG. 1A shows a schematic diagram of a pressurized fluid imaging system according to one embodiment of the present invention.

FIG. 1A shows a schematic diagram of a pressurized fluid imaging (PFI) system 1 according to one embodiment of the present invention. In one application, a sample of downhole formation fluid 24 is obtained and maintained at downhole pressure and temperature conditions. The fluid sample 24 is introduced into the sample side of buffer cells 20 and 21. Buffer cells 20 and 21 have a piston 23 with a sliding seal (not shown) for isolating the sample fluid 24 from a pressurizing fluid 25, commonly a mineral oil. The sample fluid sides of buffer cells 20 and 21 are hydraulically connected by fluid conduit 10 which may be a high pressure tubing. View cell 11 is disposed in conduit 10 such that sample fluid 24 passes through view cell 24 as sample fluid 24 is caused to flow between buffer cells 20 and 21 as described below.

The pressurizing fluid sides of buffer cells 20 and 21 are hydraulically connected to hydraulic pumps 5 and 6 respectively by conduits 50 and 51. Precision hydraulic pumps 5 and 6 are precision pumps having an internal stepper motor driven piston (not shown). Pumps 5 and 6 are controlled by controller 9. Such a pump and a controller are commercially available, for example from Quizix, Inc. of North Highlands, Calif. In one mode, one pump extends at a first predetermined rate while the other pump retracts at a second predetermined rate, thereby causing sample fluid 24 to flow between buffer cells 20 and 21. The pumps 5 and 6 may be controlled by controller 9 to cause the sample fluid 24 to flow back and forth between buffer cells 20 and 21. In operation, when the first predetermined rate is equal to the second predetermined rate, the system pressure remains substantially constant. In another mode, the first predetermined rate is less than the second predetermined rate, or vice versa, causing the system pressure to be controllably reduced or increased. Alternatively, the system pressure may be detected using pressure sensor 3. Controller 9 may be used to adjust the first and second predetermined rates to maintain the system pressure at a predetermined value. The predetermined pressure may also vary with time, with the processor adjusting the first and second rates according to programmed instructions in controller 9. When the fluid from one buffer cell is substantially all transferred to the other buffer cell, the pumps may be reversed, allowing substantially continuous flow through the view cell 11.

As shown in FIG. 1A, buffer cells 20 and 21 are positioned within thermal chamber 12 that is maintained at substantially downhole temperature using temperature sensor 4 and commercially available heaters. Alternatively, the temperature of thermal chamber 12 may be controlled such that the chamber temperature and pressure profiles are coordinated to simulate the profiles of a fluid as it is being pumped from a well.

Figure 1B:
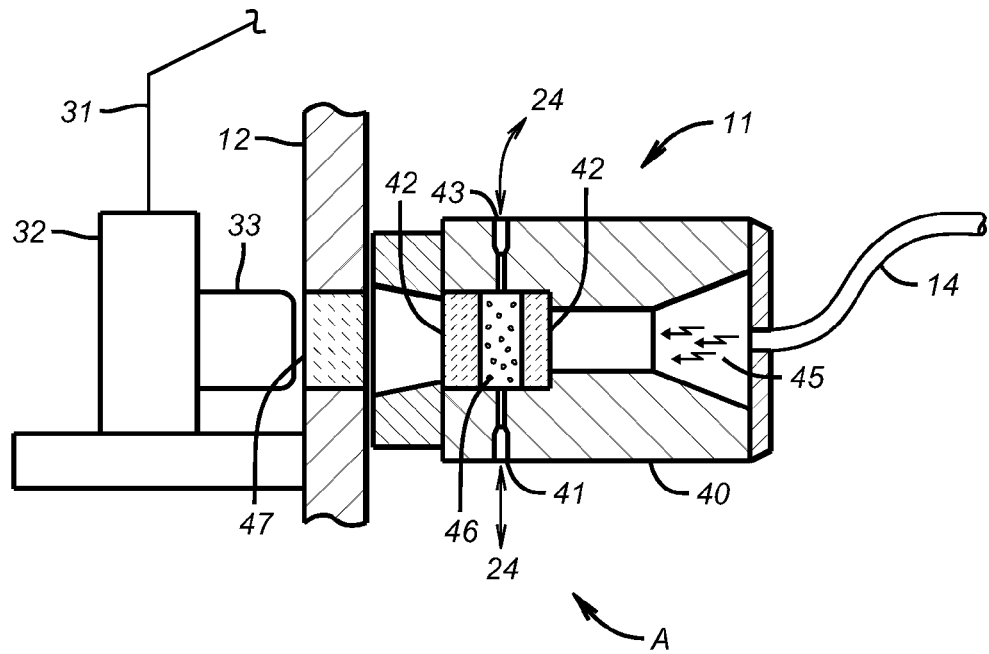
FIG. 1B illustrates detail A of FIG. 1A.

The operation of pumps 5 and 6 causes sample fluid 24 to pass through view cell 11 that is shown in more detail in FIG. 1B. As shown in FIG. 1B, view cell 11 has ports 41 and 43, in housing 40, connected to a chamber 46 having windows 42 positioned on either side of chamber 46 to allow visual examination of sample fluid 24 as it traverses, in either direction, chamber 46. Windows 42 are designed to operate with sample fluid 24 pressures of 20,000 psi. The size of chamber 46 may be adjustable to maintain a predetermined light transmission through the sample fluid 24 as the properties of the fluid samples 24 change. Such a view cell is commercially available from Temco, Inc. of Tulsa, Okla. Sample fluid 24 is illuminated in chamber 46 by light 45 from light source 13 (see FIG. 1A) transmitted to visual cell 11 along light pipe 14. Light source 13 provides light from a halogen source. Alternatively, a xenon source may be used. Both types of sources are commercially available and will not be described further. Also, in embodiments where ambient light is sufficient, then the light source can be omitted.

Light 45 passes through sample fluid 24 in chamber 46 and through window 47 in a wall of thermal chamber 12. Light 45 passes through an optical magnifier 33 and is captured by imaging detector 32. Optical magnifier 33 is a microscope that is controllable by program instructions stored in memory in processor 30. In one embodiment, optical magnifier 33 is a stereo-microscope. In one embodiment, imaging detector 32 is a digital still camera connected by cable 31 to processor 30. Processor 30 may be a personal computer of a type known in the art having a processing unit, memory, internal magnetic and/or optical storage devices, and interface circuitry to communicate with digital camera 31 and optical magnifier 33. Digital camera 31 takes images according to programmed instructions controlled by processor 30. The images may be taken at fixed time intervals at rates greater than one image per second and as fast as about 1.4 images per second. Alternatively, the images may be captured by a video camera at suitable speeds for continuous playback. The images may be correlated with readings from pressure sensor 3 and/or temperature sensor 4. The images may be stored in at least one of internal memory, internal storage media, and external storage media.

Images from digital camera 31 may be visually analyzed by programmed instructions stored in processor 30 to determine various characteristics of particles present in sample fluid 24. Such characteristics include, but are not limited to, (i) particle size, (ii) particle shape, (iii) particle size distribution, and (iv) number of particles. The analysis may be accomplished by a commercially available software product such as the Image-Pro Plus brand of analysis software by Media Cybernetics, Inc. of Silver Spring, Md. The output may be in visual, tabular, and/or graphical form. The output may be correlated to the sample fluid pressure for providing, for example, an estimate of the pressure at which asphaltenes begin to substantially precipitate. The system as described above may be adapted, using techniques known in the art, for use in a laboratory and/or a field environment.

The term "image" refers generally to a representation of one or more characteristics of particles or the fluid sample that can be analyzed with or without a suitably programmed processor. While visually inspectable images have been discussed, in certain embodiments, an imaging system can used energy waves that do no necessarily produce human cognizable images.

Figure 2:
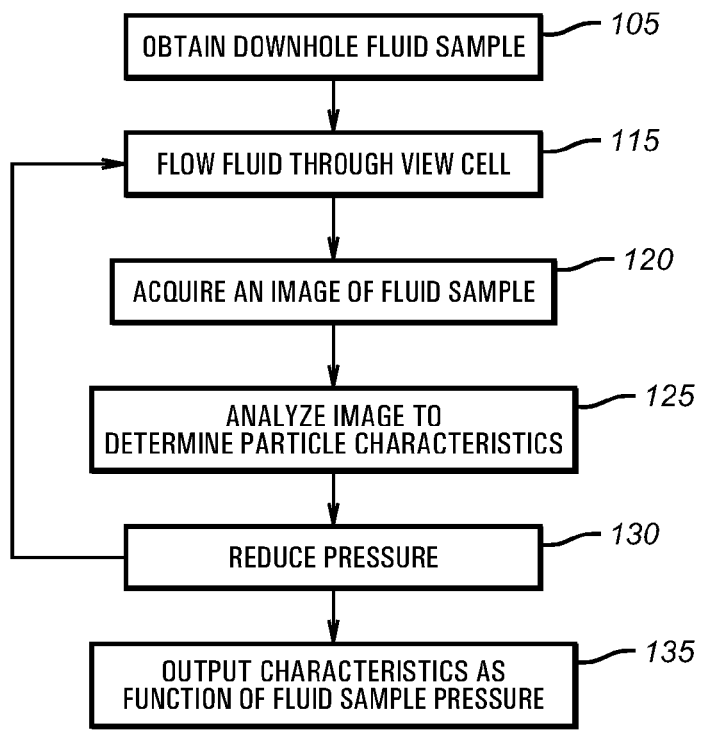
FIG. 2 illustrates a flow chart of an analysis of a fluid sample according to one embodiment of the present invention.

FIG. 2 is a flow chart of the PFI operation according to one embodiment of the invention. At step 105 a downhole fluid sample is obtained. The fluid sample is commonly kept at downhole temperature and pressure conditions during transport to the PFI. At step 115, the downhole fluid sample is caused to flow through the view cell. At least one image of the downhole fluid sample is acquired at step 120. The image is analyzed at step 125 to determine characteristics of the particles. As described previously, these characteristics include, but are not limited to, (i) particle size, (ii) particle shape, (iii) particle size distribution, and (iv) number of particles. The pressure of the fluid sample is reduced a predetermined amount in step 130. At each pressure change, steps 115 through 125 are repeated. The characteristics of the particles are output as a function of fluid sample pressure in step 135. The output may be in visual, tabular, and/or graphical form. As described previously, the downhole fluid sample may be analyzed in the laboratory or at a field location, using the system of the present invention. Alternatively, all of the images may be taken, stored, and analyzed at a later time.

It should be appreciated that the teachings of the present invention can be adapted to numerous types of testing. Implementing some of these tests may require additional components. For example, referring now to FIG. 1A, a titration test may require the use of a third pump 60 coupled to a cell 62 via a suitable line 63 to inject a second fluid 64 into the fluid sample. The second fluid can be an oil, a gas, a formation fluid, a wellbore fluid such as drilling fluid, a reagent or some other fluid. During fluid compatibility or titration testing, two or more fluids are blended together to form a resultant fluid before passing through the view cell 11. The controller 9 can be programmed to control the pumps 5, 9 and 60 to provide the desired flow rate, pressure, temperature and other parameters for performing a titration testing. Also, for filtration testing, a filter element 70 can be positioned along a flow line 72 connected to the fluid conduit 10. The flow line 72 can include suitable flow control devices 76 to selectively control flow through the flow line 72. As the fluid sample is discharged from the fluid conduit 10, the filter element 70 captures particulate in the out-flowing fluid. Using parameters such as the volume of flow through the filter and the weight of the captured particulate, characteristics such as asphaltine content can be determined. Still other tests that can be performed using embodiments and teachings of the present invention include isothermal depressurization experiments, reversibility experiments, and hysteresis experiments. The details of the above-described tests and analyses are known to those skilled in the art and will not be discussed in further detail. It should be appreciated that multiple pumps, flow conduits and other devices can be added to perform such functions.

The foregoing description is directed to particular embodiments of the present invention for the purpose of illustration and explanation. It will be apparent, however, to one skilled in the art that many modifications and changes to the embodiments set forth above are possible without departing from the scope of the invention. For instance, while embodiments of the present invention have been discussed in the context of downhole fluids, embodiments of the present invention can be used to test and analyze any fluid sample regardless of its source or origin. It is intended that the following claims be interpreted to embrace all such modifications and changes.

What is claimed is:

1. A system for determining a parameter of interest of at least one particle in a fluid sample, comprising:
    a. a view cell for viewing at least a portion of the fluid sample;
    b. an imaging device for capturing a plurality of images of the fluid sample in the view cell;
    c. a plurality of pumps cooperating to force the fluid sample to pass back and forth through the view cell, wherein the plurality of pumps are configured to change a sample pressure such that each image of the plurality of images is associated with the fluid sample at a different pressure; and
    d. a computer analyzing the at least one image to determine at least one parameter of interest of the at least one particle.

2. The system of claim 1, further comprising a temperature controlled chamber surrounding the view cell.

3. The system of claim 1, wherein the controller controls the plurality of pumps using at least one of (i) a preset pressure, and (ii) a preset temperature.

4. The system of claim 1, wherein the imaging device comprises:
    i. a microscope; and
    ii. a camera.

5. The system of claim 1, wherein the imaging device takes a plurality of images, each of the plurality of images taken at a predetermined time step.

6. The system of claim 1 wherein the at least one parameter of interest is selected from the group consisting of (i) average particle size; (ii) particle size distribution (iii) total number of particles, (iv) average part size as a function of pressure, (v) particle size distribution as a function of pressure, and (vi) total number of particles as a function of pressure.

7. The system of claim 1 wherein the plurality of pumps includes at least three pumps wherein at least one of the at least three pumps supplies a second fluid into the fluid sample.

8. The system of claim 7 wherein the second fluid is one of: (i) an oil, (ii) a gas, (iii) a formation fluid, (iv) a wellbore fluid, and (v) a reagent.

9. The system of claim 1 further comprising a fluid line coupled to the view cell, and a filter in the fluid line, the filter filtering at least a portion of the sample fluid flowing out of the view cell.

10. The system of claim 9 wherein the fluid sample is from a subterranean formation.

11. A system for determining a parameter of interest of at least one particle in a fluid sample, comprising:
    a view cell for viewing at least a portion of the fluid sample;
    an imaging device for capturing at least one image of the fluid sample in the view cell;
    a plurality of pumps cooperating to force the fluid sample to pass back and forth through the view cell; wherein the plurality of pumps includes a first pump and a second pump, a first buffer cell connected to the first pump and a second buffer cell connected to the second pump, each buffer cell being separately connected to the view cell; and
    a computer analyzing the at least one image to determine at least one parameter of interest of the at least one particle.

12. The system of claim 11, wherein the plurality of pumps are operated by a controller configured to extend the first pump while retracting the second pump.

13. A method for determining a parameter of interest of at least one particle in a fluid sample, comprising:
    a. controlling a plurality of pumps to force the fluid sample to pass through a view cell at a predetermined pressure;
    b. capturing an image of the fluid sample;
    c. changing the fluid pressure of the fluid sample;
    d. repeating steps a) through c) over a predetermined number of fluid pressure changes; and
    e. analyzing at least one captured image to determine at least one parameter of interest of at least one particle.

14. The method of claim 13, wherein the step of analyzing includes determining at least one parameter of interest selected from the group consisting of (i) average particle size; (ii) particle size distribution (iii) total number of particles.

15. The method of claim 13, wherein capturing the image includes storing the image in a computer readable storage medium.

16. The method of claim 13, wherein the at least one particle is at least one of (i) an asphaltene, (ii) an emulsion droplet and (iii) a gas bubble.

17. The method of claim 13 wherein the plurality of pumps includes at least two pumps cooperating to pump fluid through the view cell.

18. The method of claim 13 wherein the plurality of pumps includes at least three pumps wherein at least one of the at least three pumps supplies a second fluid into the fluid sample.

19. The method of claim 18 further comprising analyzing a resultant fluid formed by the second fluid and the fluid sample.

20. The method of claim 13 wherein the second fluid is one of: (i) an oil, (ii) a gas, (iii) a formation fluid, (iv) a wellbore fluid, and (v) a reagent.

21. The method of claim 13 further comprising filtering the fluid sample flowing out of the view cell.

22. The method of claim 21 further comprising analyzing a material captured during filtering.

23. The method of claim 13 wherein the fluid sample is from a subterranean formation.

* * * * *

UNITED STATES PATENT AND TRADEMARK OFFICE
CERTIFICATE OF CORRECTION

| | |
|---|---|
| PATENT NO. | : 7,542,139 B2 |
| APPLICATION NO. | : 11/487724 |
| DATED | : June 2, 2009 |
| INVENTOR(S) | : Michael Bordelon |

It is certified that error appears in the above-identified patent and that said Letters Patent is hereby corrected as shown below:

Col. 5, Claim 6, line 4:

(iv) "average part size" should be "average particle size"

Signed and Sealed this

Third Day of August, 2010

David J. Kappos
*Director of the United States Patent and Trademark Office*